United States Patent [19]

Ireland et al.

[11] Patent Number: 5,574,057
[45] Date of Patent: Nov. 12, 1996

[54] NAAMIDINE A EXTRACTED FROM SEA SPONGES AND METHODS FOR ITS USE AS AN ANTI-TUMOR AGENT

[75] Inventors: Chris M. Ireland, Sandy, Utah; Brent R. Copp, Christchurchl, New Zealand; Craig R. Fairchild, Yardley, Pa.

[73] Assignee: University of Utah Research Foundation, Salt Lake City, Utah

[21] Appl. No.: 249,688

[22] Filed: May 26, 1994

Related U.S. Application Data

[63] Continuation of Ser. No. 13,030, Feb. 3, 1993, abandoned.

[51] Int. Cl.$^6$ .................................................. A61K 31/415
[52] U.S. Cl. ............................................................ 514/390
[58] Field of Search ............................................... 514/390

[56] References Cited

U.S. PATENT DOCUMENTS

| | | | |
|---|---|---|---|
| 4,568,665 | 2/1986 | Mitchell | 514/9 |
| 4,729,996 | 3/1988 | Wright et al. | 514/215 |
| 4,737,510 | 4/1988 | Rinehart, Jr. | 514/388 |
| 4,788,190 | 11/1988 | Saksena et al. | 514/227.8 |
| 4,808,590 | 2/1989 | Higa et al. | 514/272 |
| 4,866,084 | 9/1989 | Gunasekera et al. | 514/397 |
| 4,908,363 | 3/1990 | Klotzer et al. | 514/235.8 |
| 4,970,226 | 11/1990 | Sun et al. | 514/397 |
| 5,064,657 | 11/1991 | Jackson et al. | 424/537 |

OTHER PUBLICATIONS

Carmely, et al., Naamines and Naamidines, Novel Imidazole Alkaloids From the Calcareous Sponge Leucetta Chagosensis, vol. 38, No. 26 Tetrahedron Letters, 3003–3006 (1987).

Carmely, et al., 2–Amino Imidazole Alkaloids From the Marine Sponge Leucetta Chagosensis, vol. 45, No. 7, Tetrahedron, 2193–2200 (1989).

Lyall, et al., Tyrophostins Inhibit Epidermal Growth Factor (EGF)–Receptor Tyrosine Kinase Activity in Living Cells and EGF–Stimulated Call Proliferation, vol. 264, No. 24, The Journal of Biological Chemistry, 14503–14509 (1989).

*Primary Examiner*—Jerome D. Goldberg
*Attorney, Agent, or Firm*—Workman Nydegger Seeley

[57] ABSTRACT

Naamidine A isolated from marine sponges is found to be selective in inhibiting the growth of tumor cells which are dependent upon epidermal growth factor for their growth, while showing acceptably low general cytotoxicity. Such selectivity was established through in vitro and in vivo comparative testing using tumor cells which over express EGF receptor cites. The in vivo tests used nude athymic mice that were implanted with squamous cells carcinoma.

10 Claims, 3 Drawing Sheets naamidine a

NAAMIDINE A EXTRACTED FROM SEA SPONGES AND METHODS FOR ITS USE AS AN ANTI-TUMOR AGENT

This application is a continuation of U.S. application Ser. No. 08/013,030, filed Feb. 3, 1993, now abandoned.

BACKGROUND

The research underlying the following technology was supported by NIH Grants CA 36622 and CA 50750.

1. Field of the Invention

This invention relates to the isolation of naamidine A from sea sponges and methods for its use as an inhibitor of tumor growth. In particular, the present invention relates to the use of naamidine A extracted from sea sponges to inhibit the growth of cancerous tumors, including skin cancer tumors, that are dependent upon epidermal growth factor ("EGF") for their growth.

2. Relevant Technology

A. Cancer.

Cancer is one of the most feared diseases and has claimed the lives of millions of people. Although the list of known cancer-causing agents is long, the exact causes of most cancers remain relatively unknown. However, it is known that cancer is the uncontrolled proliferation of malignant cells, which proliferation causes the progressive destruction of normal body tissue and functions and, eventually, death. This process can be slow or rapid depending on the location or nature of the cancerous tissue.

Considerable research and resources have been devoted to finding useful antitumor treatments. While methods and compositions have been developed which aid in inhibiting, remitting, or controlling the growth of tumors, new and better methods in antitumor chemical compositions are needed.

The elusive goal of most cancer treatments has been to stop the proliferation of the cancerous cells through the prohibition of cell regeneration without, at the same time, disrupting normal cell activity necessary to sustain life. This is most often attempted through the use of antineoplastic agents which interfere with the replication of the deoxyribonucleic acid ("DNA"), cause damage to the DNA, or disrupt the mitotic progression of the cancer cells.

Typical cancer treatments can generally be divided into one of the following categories: (1) antineoplastic agents, (2) hormones and steroids, (3) antiemetics, (4) anti-infectives, (5) narcotics, (6) nonnarcotic analgesics, and (7) tranquilizers. Only the first group (and to a certain extent, the second group) of treatments actually inhibits the growth of cancerous cells, while the other six serve mainly to reduce pain or relieve some of the other symptoms experienced by the cancer victim.

All of these various anticancer agents have been used with varying degrees of success. However, they all share the disadvantage that treatments that inhibit cell growth in cancerous cells extends to normal cells as well and can lead to serious and potentially life threatening side effects. Therefore, new anticancer treatments are continuously being sought which will prove to be more selective in inhibiting cancer cells, while being less toxic to the normal cells.

B. Isolation of Antitumor Agents from Marine Life.

Plants and animals have yielded a number of chemical molecules which have useful biological activity, including antitumor activity. One particularly rich source of biologically active chemicals are marine organisms, which comprise over half a million species. Marine organisms have been found to produce a variety of metabolic substances which often have unprecedented chemical structures because of their unusual living environment as compared with terrestrial organisms.

In recent years, an increasing number of natural products extracted from marine organisms have been reported to exhibit a variety of biological activities such as antimicrobial, antiviral, antifungal and anticancer activities. These include peptides, polyethers, alkaloids, prostanoids, and the like. The marine life forms that are known to have yielded useful compounds include sponges, octocorals, algae, tunicates, nuclibranches, bryozoans and marine bacteria.

Already patents have been obtained for a number of compounds extracted from marine life that have exhibited antitumor activity. U.S. Pat. No. 4,729,996 discloses antitumor compounds with imidazole rings, which were isolated from the marine sponges *Teichaxinella morchella* and *Ptioocaulis walpersi*. U.S. Pat. No. 4,808,590 discloses nitrogen containing cyclic compounds isolated from the marine sponge *Theoneloa sp.* which have antiviral, antitumor and antifungal properties. U.S. Pat. No. 4,866,084 discloses bisindole alkaloids extracted from the marine sponge *Spongosorites ruetzleri* useful in treating certain classes of tumors. U.S. Pat. No. 4,970,226 discloses bis-indole imidazole alkaloids and derivatives isolated from the marine sponge *Spongosorites sp.* which exhibit useful antitumor and antimicrobial properties.

In addition to these patents, a number of publications disclose biologically useful organic compounds derived from marine sponges, including Scheuer, P. J. (ed.) *Marine Natural Products, Chemical and Biological Perspectives* Academic Press, New York, 1978–1983, Vol. I–V; Faulkner, D. J., 1984 Natural Products Reports 1:551–598; Natural Products Reports 1986 3:1–33; Natural Products Reports 1987 4:539–576; Natural Products Reports 1988 5:613–663; J. Am. Chem. c. 1985 107:4796–4798.

C. The Isolation of Naamidine A from Marine Sponges.

Naamidine A was first isolated by Shmuel Carmely and Yoel Kasman in 1987 from the red sea sponge *Leucetta chagosensis*. See Carmely, S., et al., Naamines and Naamidines, Novel Imidazole Alkaloids From the Calcareous Sponge, *Tetrahedron Lett.*, Vol. 28, No. 26, pp. 3003–06 (1987). A structurally similar molecule, isonaamidine B, was isolated from the same sponge by Shmuel Carmely, Micha Ilan and Yoel Kashman in 1989. See Carmely, S., et al., 2-Amino Imidazole Alkaloids From the Marine Sponge Leucetta chagosensis, *Tetrahedron Lett.*, Vol. 45, No. 7, pp. 2193–2200 (1989).

Although isolated and reported, naamidine A was not known to possess any useful biological activities prior to the efforts of the present inventors. As reported in the publications listed above, this compound was merely identified in terms of its chemical structures, physical properties, and spectral characteristics. Thus, before the efforts of the present inventors this compound was unknown as a potential pharmaceutical agent. Nevertheless, because naamidine A has been isolated and characterized and is readily available it would be a significant advancement in the art relative to naamidine A if it were proved to possess biologically important properties.

In general, it will be appreciated that it would be an advancement in the art if naturally occurring compounds could be found which had antitumor properties. It would be an even more profound advancement in the art if such naturally occurring compounds exhibited selectivity such that they would inhibit the growth of cancerous cells without unduly inhibiting the growth or activity of normal cells such that they would not result in the death of the organism being treated.

Finally, it would be an advancement in the art if naamidine A could be used to selectively inhibit the growth of cancerous cells without unduly inhibiting the growth or activity of normal tissue cells.

Such teachings and methods are disclosed and claimed herein.

BRIEF SUMMARY AND OBJECTS OF THE INVENTION

The present invention involves the use of a compound extracted from marine sponges, namely naamidine A, in inhibiting tumor activity. In particular, naamidine A has been shown to selectively inhibit the growth of cancerous cells dependent on epidermal growth factor ("EGF") for their growth, while not unduly inhibiting the activity of normal cells if administered in proper doses.

Naamidine A is the common name for a compound within the class of compounds known as 2-amino imidazole alkaloids. The naamidine A that was collected and used in the experiments leading up to the discovery of its usefulness as an antitumor agent was isolated from the calcareous sponge *Leucetta chagosensis* collected from the shallow reef sites off Dravuni Island in the Fiji Island group. Voucher specimens have been deposited in the Scripps Institute of Oceanography Benthic Invertebrate collection.

Figure 1:
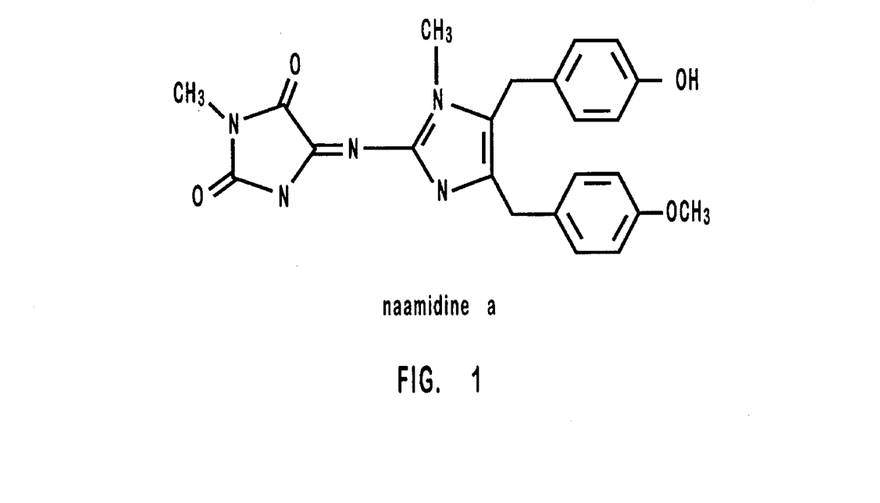
FIG. 1 shows the deduced structure of the naamidine A.

The isolation of naamidine A was performed using solvent partition and countercurrent chromatography. The final purification of the compounds was achieved using HPLC. The chemical structures were determined mainly on the basis of their $^1$H and $^{13}$C nmr data and mass and IR spectra. The deduced structure of naamidine A is shown in FIG. 1.

Naamidine A is particularly useful in inhibiting the proliferation of cancer cells that are dependent upon EGF for growth. Preliminary tests have shown that naamidine A has exhibited relatively low general in vitro cytotoxicity, as well as being less potent in inhibiting insulin stimulated cell proliferation compared to EGF stimulated growth. This specificity by naamidine A toward inhibition of EGF activity in cancerous cells is extremely useful because it indicates that naamidine A may not interfere with the normal growth and well being of regular, noncancerous body cells which are not EGF growth dependent.

The assay to determine a compound's selectivity compares the level of inhibition of the targeted activity (EGF stimulation of cell growth) with the inhibition of insulin stimulated cell growth. A base line level for minimum specificity is met when a compound is 10 times more selective in inhibiting the targeted activity than in inhibiting the activity of insulin. Naamidine A was shown in preliminary testing to be about 22 times more selective in inhibiting EGF dependent growth relative to insulin dependent growth as measured by tritiated thymidine incorporation.

Subsequent in vivo tests have confirmed that naamidine A is capable of inhibiting the growth of cancerous cells dependent on EGF for their growth without killing the organism (the mouse) being treated. In particular, a human squamous cell carcinoma that over expresses the EGF receptor that was implanted into athymic mice was used to determine the potential medicinal qualities of naamidine A.

In a first test, the mice were treated with varying dosages of naamidine A for five days beginning the day after implantation of the carcinoma. Tumor growth was assessed by measuring the change in tumor size over a fifteen day period. Although naamidine A inhibited tumor growth, the inhibition was a modest 37%. Therefore, a second evaluation was carried out using a different schedule of treatment and evaluation.

In this test, the mice were treated with varying dosages of naamidine A for five days after implantation of the carcinoma. The tumors were then evaluated for growth activity seven days after implantation, as determined by the change in tumor size. Tumor growth was inhibited by about 85% when somewhat toxic doses were used. Although moderately toxic dosages were required to achieve the best results, the tests did establish that naamidine A is able to significantly and selectively inhibit the growth of cancer cells dependent upon EGF for their growth, while not destroying the organism being treated. The best results were obtained using doses of about 25 mg naamidine A per kilogram of mouse body mass.

Although the exact mechanism of how naamidine A inhibits EGF growth stimulation is not known, it is possible that it interferes with some step in the signal transduction pathway which leads to cell proliferation. Studies have shown that naamidine A does not appear to affect the binding of EGF to its corresponding receptor cite in the cancer cell, even at high concentrations (500 µg/ml).

Using extrapolation techniques presently accepted in the field of testing pharmaceutical drugs on laboratory animals, it has been determined that proper doses of naamidine for humans might be as low as 0.08 mg and as high as 500 mg per kilogram of human body mass.

From the foregoing, it will be appreciated that an object of the present invention is to find natural compounds that have been extracted from marine life which can be used to treat cancer. Another object and feature of the present invention is to discover natural compounds which are able to selectively inhibit the growth of cancerous cells without unduly inhibiting normal cell activity.

Another object and feature of the present invention is to find natural compounds extracted from marine life which are specific in inhibiting the growth of cancerous cells that are dependent on EGF for their growth, without being generally cytotoxic or interfering with the normal activity and growth of normal tissue cells.

More specifically, an object of the present invention is to find proper dosages and treatment protocols such that naamidine A can selectively inhibit the growth of cancerous cells without unduly inhibiting the growth or activity of normal tissue cells.

These and other objects and features of the present invention will become more fully apparent from the following description and appended claims, or may be learned by the practice of the invention.

DETAILED DESCRIPTION OF THE PREFERRED EMBODIMENTS

A. Isolation and Characterization of Naamidine A.

The present invention pertains to the extraction of naamidine A from marine sponges and its use as an antitumor agent. Based on presently accepted extrapolation techniques, the present invention also generally discusses possible pharmaceutically suitable doses of naamidine A, as well as possible methods of administration, albeit in broad, general terms. The amounts and methods of administration are based on tests of naamidine A on laboratory mice, as set forth more fully below.

Naamidine A was originally isolated from the calcareous sponge *Leucetta chagosensis* collected in the Gulf of Eilat in the Red Sea and belongs to the class Calcisponginae. Although the isolation and structural determination of this compound has been previously reported, until the efforts underlying the present invention, it was not known that naamidine A had any useful biological uses. In particular, it was not known that naamidine A was useful as an anticancer agent, that it was selective in inhibiting the growth of cancer cells dependent on EGF for their growth, or which doses and through which methods of administration naamidine A would be useful.

The extraction of naamidine A from sea sponges, its isolation, its structure (shown in FIG. 1), and the various tests used to determine its structure and other physical properties are all set forth in detail in Carmely, S. et al., "Naamines and Naamidines, Novel Imidazole Alkaloids From the Calcareous Sponge," *Tetrahedron Lett.*, Vol. 28, No. 26, pp. 3003–06 (1987) and Carmely, S., et al., "2-Amino Imidazole Alkaloids From the Marine Sponge Leucetta chagosensis," *Tetrahedron Lett.*, Vol. 45, No. 7, pp. 2193–2200 (1989). For purposes of disclosure, the foregoing articles are incorporated herein by specific reference.

The naamidine A isolated and used in the context of the present invention was extracted from a sponge of the same genus as the Red Sea sponge described by Carmely and Kashman, although the class of this sponge has not been determined or named at this time. The sponge samples used in the present invention were collected from shallow reef sites off Dravuni Island in the Fiji Island Group in 1984 and kept frozen until they were more recently tested. A voucher specimen has been deposited in the Scripps Institute of Oceanography Benthic Invertebrate Collection.

The naamidine A was extracted from the sponges through a series of different extraction procedures and methods. First, sponge specimens (400 g) were extracted through repeated iterations with methanol-chloroform and water. The chloroform layers were combined and then partitioned by counter current centrifugation on isopropylamino support using a stepped gradient of hexane-chloroform and chloroform-methanol solvent mixtures. The 90% chloroform-10% methanol fraction contained 32 mg of naamidine A, which was further purified by isopropyl-amino high pressure liquid chromatography using 95% chloroform-5% methanol eluent.

The molecular formula, molecular structure (FIG. 1), and molecular weight of naamidine A used in the context of the present invention were determined by means of a series of tests using IR, UV, nmr and mass spectra. The molecular formula of naamidine A ($C_{23}H_{23}N_5O_4$) and molecular weight (433) were determined by means of High Resolution Electron Ionization Mass Spectrometer (HREIMS).

Proton connectivities were established by means of a long-range COSY45 nmr spectra. It was determined from the results of the spectrum obtained by this nmr test that the methylene resonance at 3.51 ppm was benzylic to a paraphenol spin system (atoms 1' to 5' in FIG. 1), while the methylene protons observed at 3.66 ppm were benzylic to a para-anisole system (atoms 7 to 11). The two remaining methyl signals yielded no long-range proton-proton coupling information.

Direct proton-carbon connectives were established by means of an HMQC nmr spectra.

Long-range proton-carbon connectives were established by means of an HMBC nmr spectra. The HMBC nmr spectra confirmed the placement of the methylene bridge protons to their respective para-substituted benzoid rings, and also established connectives between these spin systems and positions 4 and 5 of the 2-amino imidazole moiety. The exact placement of the para-phenol moiety to the 5 position of the 2-amino imidazole was achieved by the observation of long-range correlations from the imidazole N-methyl (3.10 ppm) to imidazole positions 2 and 5. The remaining N-methyl resonance (2.69 ppm) exhibited long-range correlations to carbon resonances at 159.38 and 163.96 ppm, thus unequivocally assigning them as carbons 2" and 5". The remaining carbon resonance (150.79 ppm) was assigned to position 4" due to the lack of correlations observed and for chemical shift considerations. This completed the structural assignment of naamidine A.

1-D difference NOE nmr experiments provided further confirmation of the position of the imidazole N-methyl (3.10 ppm) relative to the para-phenol substituent. Irradiation of 1-$NCH_3$ resulted in enhancement of the 1' methylene resonance at 3.51 ppm (1.2%), as well as the 3' ortho-benzoid protons at 6.68 ppm (0.8%).

Naamidine A was also analyzed using a variety of other spectral techniques. Ir spectra were recorded on a PerkinElmer 1600 FTIR spectrophotometer. UV spectra were recorded on a Bechman DU-8 spectrophotometer. $^1H$ and $^{13}C$ nmr spectra were obtained at 500 and 125 MHz, respectively, on a Varian Unity 500 spectrometer, in a 1:1 solvent mixture of deuterated benzene and deuterated methanol. All spectra were referenced to residual benzene signals ($^1H$: 7.15 ppm; $^3C$: 128.00 ppm). Mass spectra were obtained on a Finnigan MAT 95 mass spectrometer.

The summary of the spectral data upon which naamidine A was characterized are as follows: Yellow solid: eims {M+} 433 (100%); HREIMS {M+} 433.1746); $C_{23}H_{23}N_5O_4$ requires 433.1750 ($\Delta$0.4 mmu); FTIR $\Delta_{max}$ (smear) 3332.1, 2929.3, 1731.7, 1567.7, 1514.0, 1454.4, 1248.2, 1154.7, 1034.7, 754.9 cm$^{-1}$; UV $\lambda_{max}$ ($CHCl_3$) 240.5 nm ($\epsilon$ 19 900), 277.2 (7 100), 390.9 (15 500), 418.0 (11 300); $^1H$ nmr (500 MHz, 1:1 $C_6D_6/CD_3OD$) 7.01 (2H, d, J=8.5 Hz, H-9), 6.78 (2H, d, J=8.5 Hz, H-4'), 6.71 (2H, d, J=8.5 Hz, H-10), 6.68 (2H, d, J=8.5 Hz, H-3'), 3.66 (2H, s, H-7), 3.51 (2H, s, H-1'), 3.42 (3H, s, 11-$OCH_3$), 3.10 (3H, s, 1-$NCH_3$), 2.69 (3H, s, 1"-$NCH_3$); $^{13}C$ nmr (125.7 MHz, 1:1 $C_6D_6/CD_3OD$), 163.96 (s, C-5"), 159.38 (s, C-2"), 158.96 (s, C-11), 156.77 (s, C-5'), 150.79 (s, C-4"), 146.35 (s, C-2), 132.89 (s,C-4), 131.50 (s, C-8), 129.79 (2C, d, J=159 Hz, C-9), 129.38 (2C, d, J=156 Hz, C-3'), 128.25 (obscured by solvent, C-2'), 127.09 (s, C-5), 116.01 (2C, d, J=159 Hz, C-4'), 114.35 (2C, d, J=159 Hz, C-10), 54.90 (q, J=142 Hz, 11-$OCH_3$), 31.36 (t, J=127 Hz, C-7), 29.41 (q, J=142 Hz, 1-$NCH_3$), 28.32 (t, J=127 Hz, C-1'), 23.95 (q, J=140 Hz, 1"-$NCH_3$).

B. EGF and the Inhibition of Cancer Cell Growth.

The EGF receptor signal pathway is recognized as an important pathway in the development of some human tumors. over expression of the EGF receptor in certain tumor types is related to cell growth and tumorigenicity. Sporn, M. B. et al., "Autocrine Growth Factors and Cancer," *Nature*, 313:745–47 (1985); Lau, L. F., "Growth Factors and Growth Control," *Curr. Opin. Cell Biol.,* 2:280–84 (1990); Libermann, T. A. et al., "Amplification, Enhanced Expression and Possible Rearrangement of EGF Receptor Gene in Primary Human Brain Tumors of Glial Origin," *Nature* 313:144–47 (1985); Lin, C. R. et al., "Expression Cloning of Human EGF Receptor Complementary DNA: Gene Amplification and Three Related Messenger RNA Products in A431 Cells," *Science,* 224:834 (1984). For purposes of disclosure, the foregoing articles are incorporated herein by specific reference.

A great deal of work has gone into the partial elucidation of EGF signal transduction and its link to the proliferation of certain kinds of cancer cells. TGFα, a physiological ligand for the EGF receptor, is secreted by malignant as well as normal cells and has been implicated as an autocrine growth factor in tumor cells in vivo. Stromberg, K. et al., "Transforming Growth Factor-α Acts as an Autocrine Growth Factor in Ovarian Carcinoma Cell Lines," *Cancer Res.,* 52:341–47 (1992). For purposes of disclosure, this article is incorporated herein by specific reference.

The EGF receptor is a transmembrane protein of 170 kDa composed of an extracellular EGF binding domain and an intracellular protein tyrosine kinase domain which catalyzes the EGF-dependent tyrosine phosphorylation of various protein substrates as well as autophosphorylation of the EGF receptor. An EGF-receptor point mutant in which lysine 721 in the kinase domain was replaced by an alanine residue was unable to catalyze tyrosine phosphorylation in vitro and in living cells, or to stimulate DNA synthesis and cellular proliferation. Activation of the receptor tyrosine kinase by EGF is, therefore, a crucial signal that initiates the multiple cellular responses that culminate in DNA synthesis and cellular proliferation. A similar conclusion has been reached for the insulin-receptor and other protein tyrosine kinases. Lyall et al., "Tyrphostins Inhibit Epidermal Growth Factor (EGF) Receptor Tyrosine Kinase Activity in Living Cells and EGF-stimulated Cell Proliferation," *J. Biological Chem.,* 264:14503–14509 (1989). For purposes of disclosure, this article is incorporated herein by specific reference.

It has been found that compounds which interfere with EGF binding to its receptor or at some point along the signal pathway, such as the receptor tyrosine kinase, would have utility as antiproliferative agents in tumors which are dependent on EGF for growth. Indeed, antibodies against the EGF receptor have been shown to inhibit tumor cell growth both in vitro and in vivo. Kawamoto T. et al, "Growth Stimulation of A431 Cells by Epidermal Growth Factor: Identification of High-affinity Receptors for Epidermal Growth Factor by an Anti-receptor Monoclonal Antibody, " *Proc. Natl Acad. Sci. U.S.A.,* 80:1337–41 (1983); Masui, H. et al., "Growth Inhibition of Human Tumor Cells in Athymic Mice by Antiepidermal Growth Factor Receptor Antibodies," *Cancer Res.,* 44:1002–07 (1984). For purposes of disclosure, the foregoing articles are incorporated herein by specific reference.

Furthermore, the tyrphostin class of tyrosine kinase inhibitors have been found to block the proliferation of squamous cell carcinoma cells both in vitro and in vivo. Lyall et al , supra; Yoneda, T. Y. et al., "The Antiproliferative Effects of Tyrosine Kinase Inhibitors Tyrphostins on a Human Squamous Cell Carcinoma In Vitro and in Nude Mice," *Cancer Res.,* 51:4430–35 (1991). For purposed of disclosure, the foregoing articles are incorporated herein by specific reference.

An in vitro bioassay, called the EGF mitogenic assay, was used to aid in the identification of antagonists of EGF dependent cell proliferation. The mitogenic response due to EGF is quantified by measuring the incorporation of $^3$H-thymidine into NIH3T3 cells (or "EC25 cells") that have been transfected with the EGF receptor gene. Stimulation of these cells with insulin is used as a "nonspecific" mitogen control. Samples were preincubated with the EC25 cells for one hour before the addition of the mitogen, then further incubated for 16 hours, and mitogenic stimulation assessed by a one hour incorporation of $^3$H-thymidine. The development of the EC25 cell line, and the EGF mitogenic assay in which it is used, is explained in greater detail in Velu, T. J. et al., "Epidermal Growth Factor-Dependent Transformation by a Human EGF Receptor Proto-Oncogene, " *Science* 238:1408–10 (1987). Fur purposes of , disclosure, this article is incorporated herein by specific reference.

The concentration at which control insulin stimulation is inhibited 50% by the test sample ($IC_{50(insulin)}$) was calculated as was the same value for EGF ($IC_{50(EGF)}$). These values were then used to calculate a specificity ratio which is $IC_{50(insulin)}/IC_{50(EGF)}$.

The criteria for an active sample is a specificity ratio of >10 and an $IC_{50(EGF)}$>1/100 or 30 μg/ml for pure compounds. These activity criteria help determine which inhibitors are specific for the EGF signalling pathway.

C. In Vitro Testing of Naamidine A.

Experimental Test 1. A crude extract of the calcareous sponge Leucetta obtained off the coast of Fiji (which contains naamidine A) was found to be noncytotoxic ($IC_{50}$=1/64) against a human colon carcinoma cell line (HCT116) using a crystal violet cell staining assay. The crystal violet cell staining assay is explained in greater detail in Catino, J. J. et al, "A Microtitre Cytotoxicity Assay Useful for the Discovery of Fermentation-derived Antitumor Agents," *Cancer Chemotherapy Pharmacology,* 15:240–43 (1985). For purposes of disclosure, this article is incorporated herein by specific reference.

The crude naamidine A did not show any significant antimicrobial activity using the following assays: rec+, recdiff and *E-coli,* SOS/DNA damage. These assays are explained in greater detail in the following articles, respectively: Kada, T. et al, "In Vitro and Host Mediated "Recassay" Procedures for Screening Chemical Mutagens; and Phloxine, a Mutagenic Red Dye Detector," *Mutation Res.,* 16:165–74 (1973); and Mamber, S. W. et al, "The Escherichia Coli K12 SOS Chromotest Agar Spot Test for Simple, Rapid Detection of Genotoxic Agents," *Mutation Res.,* 171:83–90 (1986). For purposes of disclosure, the foregoing articles are incorporated herein by specific reference.

Experimental Test 2. The crude extract of naamidine A was tested next in the EGF mitogenic assay to determine if it might have inhibitory activity against EGF-induced mitogenesis in EC25 cells. The crude extract demonstrated activity in the EGF mitogenic assay ($IC_{50(EGF)}$=1/104 and $IC_{50(insulin)}/IC_{50(EGF)}$ ratio=10.5). Thus, an activity was identified in the crude sponge extract which demonstrated specificity toward inhibiting EGF stimulated growth.

Experimental Test 3. Several fractions of the sponge extract as well as pure naamidine A were tested in the EGF mitogenic assay. Although the less pure fractions were not active in the EGF assay, the pure sample of naamidine A showed very good activity ($IC_{50(EGF)}$=4.8 μg/ml; $IC_{50(insulin)}$=105.6 μg/ml; $IC_{50(insulin)}/IC_{50(EGF)}$ ratio=22). The results from one of these assays is shown in the graph in FIG. 2.

Figure 2:
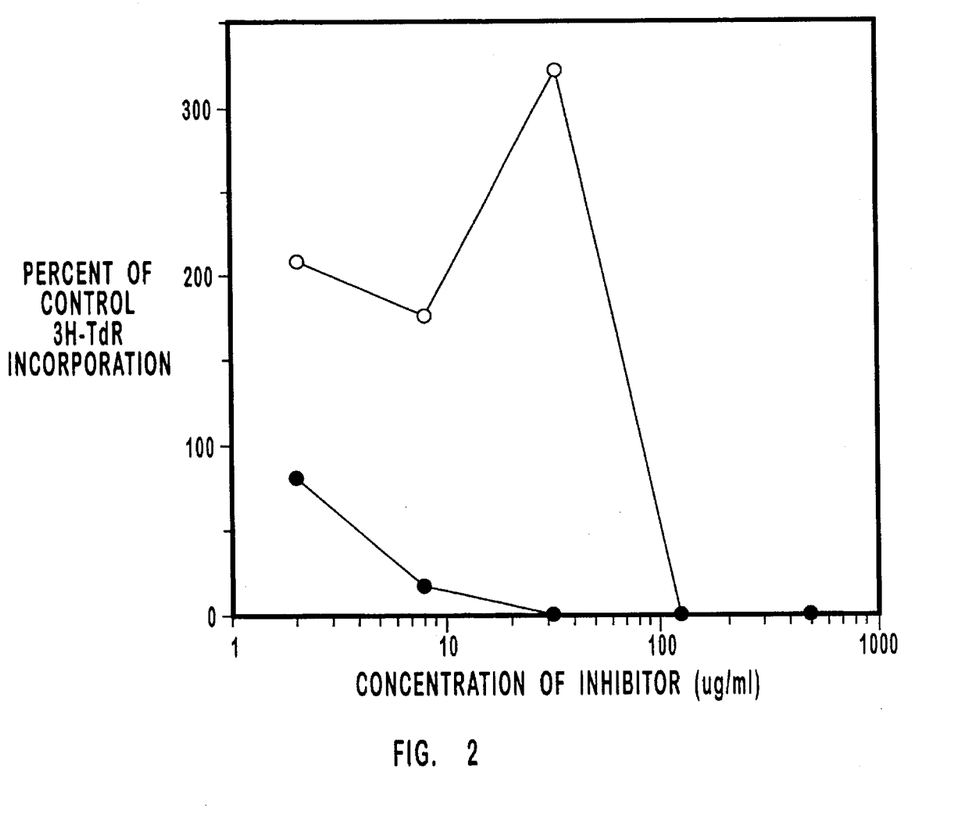
FIG. 2 is a graph comparing the inhibitory effects of naamidine A with respect to either EGF-induced or insulin-induced DNA synthesis.

FIG. 2 shows the ability of various concentrations of naamidine A to inhibit tritiated thymidine incorporation after EGF stimulation (solid circles ●) or insulin stimulation (open circles ○). The data suggest that naamidine A is potent in inhibiting the EGF signaling pathway and is more specific for the EGF mediated mitogenic response than for the insulin mediated mitogenic response.

Experimental Test 4. Presently, the mechanism of action of naamidine A for inhibition of the EGF signalling pathway is unknown. In order to investigate this, A431 cells were treated with varying concentrations of naamidine A. According to this test, naamidine A did not appear to effect the binding of EGF to receptor sites within A431 cells, even at a concentration of 500 μg/ml, as shown in the graph in FIG. 3. This assay measured the ability of naamidine A to compete with the binding of biotinylated EGF to the EGF receptor, which is highly over expressed in A431 human squamous cell carcinoma cells.

Figure 3:
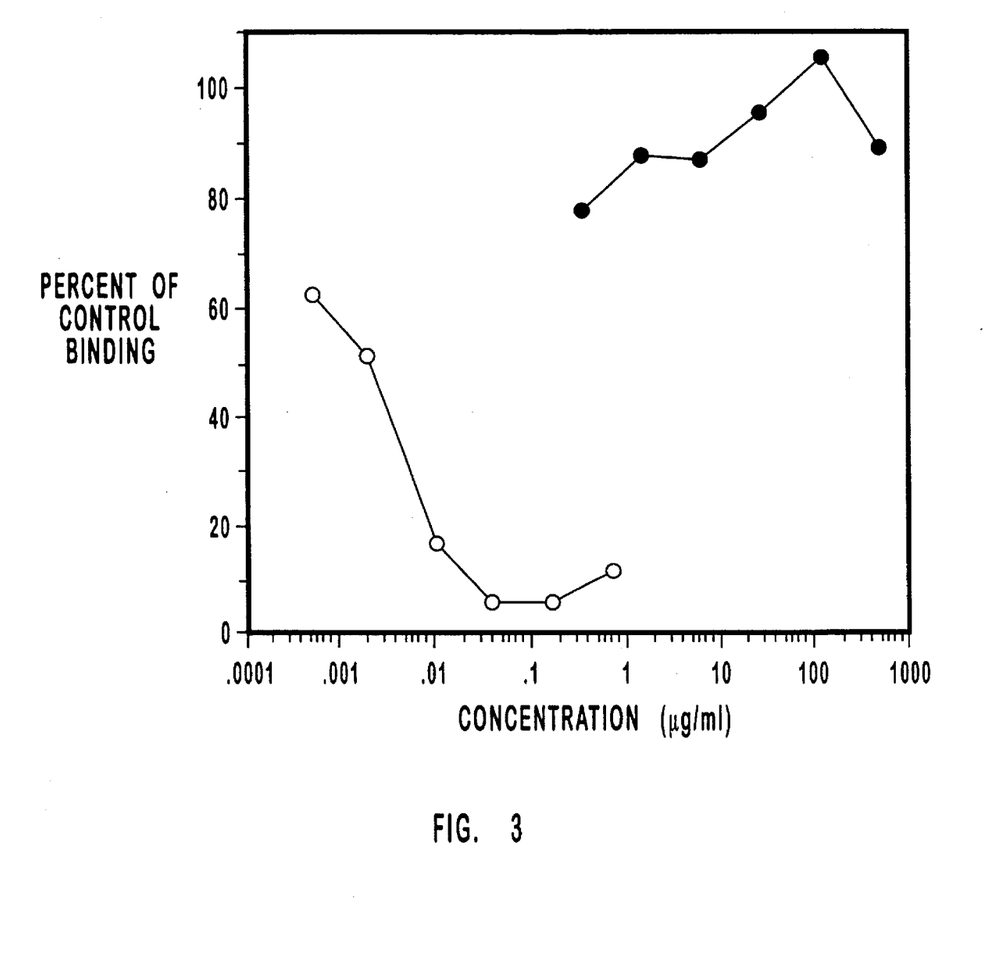
FIG. 3 is a graph comparing labeled EGF binding to its receptor sites in the presence of either naamidine A or labeled EGF.

In the assay represented in FIG. 3, the A431 cells were incubated in the presence of either the EGF standard or naamidine A plus biotinylated EGF for one hour and the degree of inhibition of biotinylated EGF binding to the EGF receptor was quantified using a peroxidase-linked anti-biotin antibody. The solid circles (●) in FIG. 3 represent the level of binding of EGF to cell receptors when the cells are subjected to various levels of naamidine A. The open circles (○) represent the level of binding of EGF to cell receptors when the cells are subjected to various levels of EGF, which is used as a positive control.

Figure 4:
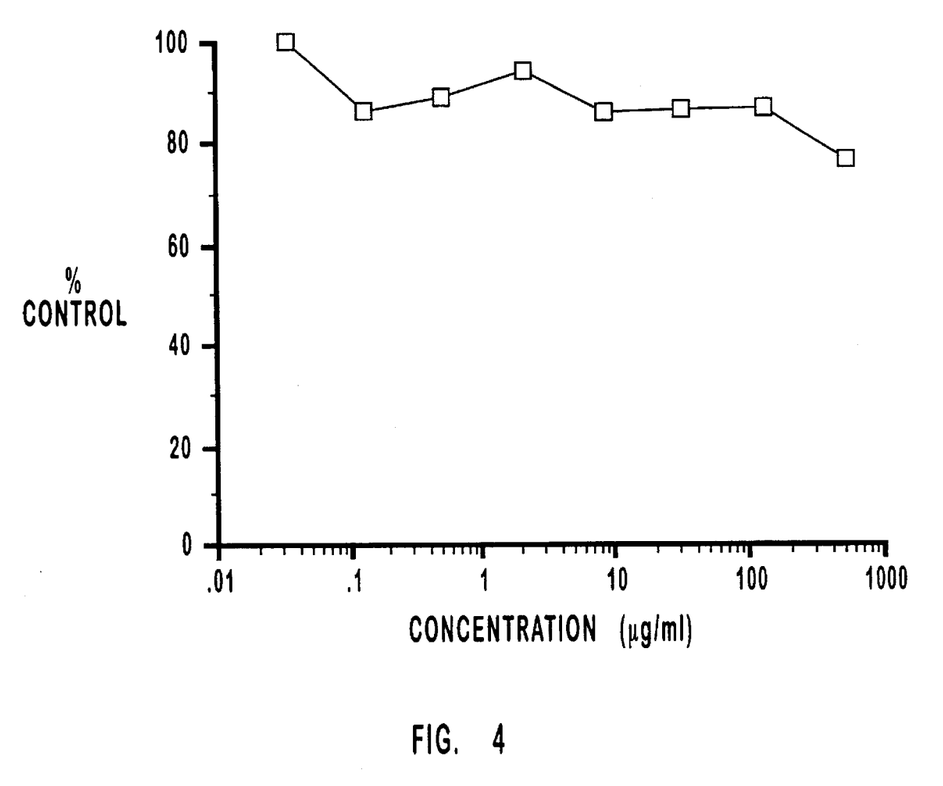
FIG. 4 is a graph showing the lack of c-src tyrosine kinase activity by naamidine A.

Experimental Test 5. Although tyrosine kinase activity is a potential target for the action of naamidine A, this compound was shown to not inhibit the activity of the isolated c-src tyrosine kinase, as shown in FIG. 4. In this assay, phosphorylation of the substrate RCM (reduced, carboxyamidomethylated and maleylated) lysozyme by c-src is quantified using a peroxidase-linked anti-phosphotyrosine antibody to determine the activity of this kinase. Cleaveland, J. S. et al., "A Microtiter-based Assay for the Detection of Protein Tyrosine Kinase Activity" *Anal. Biochem.*, 190:249–53 (1990) For purposes of disclosure, this article is incorporated herein by specific reference.

The sample of naamidine A was incubated with the substrate RCM lysosome, c-src enzyme, and ATP for 30 minutes, after which time the reaction was terminated and tyrosine phosphorylation was assessed using a peroxidase-linked antiphosphotyrosine antibody. There was no significant inhibition of c-src tyrosine kinase activity as seen in FIG. 4. By way of comparison, staurosporine, a standard reference and a potent nonspecific protein kinase inhibitor, gave an $IC_{50}$ of 7.8 μg/ml in this assay.

Experimental Test 6. To determine its general cytotoxicity, naamidine A was examined in HCT116 colon cells using an XTT(2,3-bis(2-methoxy-4-nitro-5-sulfophenyl)-5-[(phenylamino) carbonyl]-2H-tetrazdium hydroxide) dye conversion assay to measure cell proliferation. The XTT dye conversion assay is explained in detail in Scudiero, D. A. et al., "Evaluation of a Soluble Tetrazolium/Formazan Assay for Cell Growth and Drug Sensitivity in Culture Using Human and Other Tumor Cell Lines," *Cancer Res.*, 48:4827–33 (1988). For purposes of disclosure, this article is incorporated herein by specific reference.

In the XTT assay, cells are plated at 4000 cells/well in 96 well microtiter plates; 24 hours later the test drugs are added and serially diluted. The cells are incubated at 37° C. for 72 hours, at which time the tetrazolium dye, XTT, is added. A dehydrogenase enzyme in live cells reduces the XTT to a form that absorbs light at 450 nm which can be quantitated spectrophotometrically. The greater the absorbance the greater the number of live cells. The results are expressed as an $IC_{50}$ which is the drug concentration required to inhibit cell proliferation (i.e., absorbance at 450 nm) to 50% of that of untreated control cells. Test samples are considered noncytotoxic if the $IC_{50}$ in the XTT assay is greater than 20 μg/ml.

Using the XTT assay, the $IC_{50}$ for naamidine A was determined to be 31 μg/ml, which is above this established activity criteria for a cytotoxic agent.

D. In Vivo Testing of Naamidine A.

In vivo testing of naamidine A was performed to measure its ability to inhibit the growth of EGF-dependent tumors in nude mice. The model system used for these in vivo studies was a human squamous cell carcinoma (A431) that over expresses the EGF receptor, which was implanted into athymic mice. A detailed description of the A431 tumor xenograft as an in vivo model for testing a compound's ability to inhibit tumor cells dependent on EGF can be found in Robinson et al., "Characterization of the A431 Tumor Xenograft as an In Vivo Model for Testing Epidermal Growth Factor-Receptor Antagonists," *Intl. J. Oncology*, 1:293–298 (1992). For purposes of disclosure, this article is incorporated herein by specific reference. The test used by Robinson is a model which can be used to attempt to predict drug activity in humans and can be used by those skilled in the art to predict whether a particular drug might have utility in treating cancer in humans based on the drug's activity in treating mice injected with human carcinoma cells whose growth is dependent on EGF.

According to Robinson et al., the A431 cell line was adapted to grow in female athymic mice by s.c. inoculation of $10^7$ cultured cells into the axillary region. Tumors were passaged in female athymic mice by sterile dissection of solid tumors and s.c. implantation of tumor fragments into the axillary region.

Subrenal capsule (SRC) implantation of A431 tumors was performed using male mice. Following anesthesia with pentobarbital (60 mg/kg ip) the left kidney was exteriorized through a 1 cm incision using sterile procedures. A fragment of approximately 1 mm$^3$ was implanted under the renal capsule using a 20 gauge trochar and the xenograft measured (initial tumor size, "ITS") in 2 dimensions using a microscope and ocular micrometer scale. The kidney was reinserted and the wound closed with clips.

Following termination of the study the tumor fragment size was remeasured (final tumor size, "FTS"). Tumor size was calculated as length times width. Tumor growth was calculated as FTS/ITS. The tumor volume doubling time (TVDT) for the A431 tumor in this model was about 5 days, so that over the course of the 15 day experiment the tumor would double 3 times. Drug effects were calculated as the mean % inhibition the drug treatment produced on tumor growth when compared to control. Inhibition of >80% of tumor growth was considered a working criteria for "active". When FTS was smaller than ITS for a drug treated group the result was expressed as % regression by calculating the % decrease in tumor size compared to ITS. The study results for naamidine A were obtained in two experiments. Experimental Test 7. In a first in vivo experiment, the mice were treated with naamidine A at various doses (1.6 to 100 mg of naamidine per kilogram of mouse body mass, expressed as "mg/kg") once a day for five days beginning on the first day after tumor implantation (q1 d×5; 1).

The effect of naamidine A on the tumor was assessed 15 days after tumor implantation and there were six mice per treatment group. As shown in Table 1, the highest dose (100 mg/kg) was toxic to the mice and at the maximally tolerated dose (25 mg/kg) growth o f the tumor was inhibited 37%. However, to be considered active a test compound should be able to produce an inhibition of tumor growth of at least 85%.

TABLE 1

| Growth Inhibition Agent | Dose & Schedule | % Inhibition |
| --- | --- | --- |
| Naamidine A | 100 mg/kg (qld × 5;1) | toxic (multiple deaths) |
| | 25 | 37.1 |
| | 6.25 | 32.2 |
| | 1.6 | 36.6 |

Based on the results of the first in vivo test (Experimental Test 7), it was postulated that naamidine A was perhaps more cytostatic than cytotoxic. Thus, when the treatment was stopped the tumor could have resumed growing over the remaining 10 days. The result would be a net 30–40% reduction in tumor cell growth, because of the period of regrowth. Therefore, a second in vivo test was designed that would measure the growth of the tumor closer to the time in which the administration of naamidine A was halted.

Experimental Test 8. In this second in vivo test, the length of time for tumor growth was shortened to seven days to more closely coincide with the time of drug treatment. Two groups of twelve mice each were treated with the standard antibody (MA225), while there were six mice per group treated with varying doses of naamidine A.

The tumor was exposed to the test agent (naamidine A) once a day for 5 days (q1 d×5; 1), which was nearly the entire length of the growth period of 7 days. During this time, the tumor would normally be expected to double about 1.5 times instead of 3 times for a 15 day period.

Under these conditions, doses ranging from 0.78 mg/kg to 50 mg/kg were given using the same dosing schedule as with the first experiment. As shown in Table 2, an active criteria of at least 85% growth inhibition was reached, at the dose of 25 mg/kg, which can be considered the maximal tolerated dose.

TABLE 2

| Growth Inhibition Agent | Dose & Schedule | % Inhibition |
| --- | --- | --- |
| Naamidine A | 50 mg/kg (qld × 5;1) | 96.4 (2 deaths) |
| | 25 | 87.4 (1 death) |
| | 12.5 | 52 |
| | 6.25 | −7.5 |
| | 3.13 | 35 |
| | 1.56 | 47.9 |
| | 0.78 | 15.1 |

Based on these in vivo test results performed in the laboratory, it is acceptable using extrapolation techniques accepted in the field of pharmaceutical testing to make a general prediction of broad ranges of doses which may have utility for treating cancer in humans. It should be noted that although the mice involved in the in vivo testing were given naamidine A once a day, it might be preferred to administer the drug to humans in more frequently administered and smaller doses.

In terms of the amount of drug that should be administered, reference can be made to the varying amounts of drug given to the mice. In general, when initially testing a drug on humans, a starting dose is often the LD-10 value (the dose at which 10% of the mice died), divided by 30. According to Experimental Test 8, a dose of 50 mg/kg was toxic to many of the mice, while a dose of 25 mg/kg resulted in the death of one mouse. Thus, 25 mg/kg is roughly the LD-10 of naamidine based on Experiment Test 8. Based on this, a beginning dose might be about 0.8 mg of naamidine A per kilogram of patient body mass ("mg/kg"). From there, succeeding doses are increased to determine the highest possible dose before the drug becomes toxic or where the effectiveness of the drug peaks out so that higher doses do not increase the effect of the drug. In this case, the highest tolerable doses may be estimated to be in the range from between about 25 mg/kg to about 50 mg/kg.

Nevertheless, because of differences between how a mouse might metabolize the drug compared to humans, the proper dose of naamidine A might differ by a factor of ten in either direction. The dose will tend to be higher if humans metabolize (or rid the body of) naamidine A faster than mice, or lower if humans metabolize the drug more slowly. Selection of a suitable dose and protocol for administration is well within the skill of one of ordinary skill in the art.

Based on the foregoing, it is anticipated that the lowest possible doses of naamidine A which still demonstrated utility might be as low as 0.08 mg/kg or as high as 8.0 mg/kg. At the other extreme, the highest tolerable dose might be as low as 5 mg/kg or as high as 500 mg/kg. Thus, the preferable dose of naamidine A might be anywhere within the range from between about 0.08 mg/kg to about 500 mg/kg. If, instead, a direct correlation between the metabolisms of mice and humans is assumed for naamidine A, the minimum effective dose of naamidine A would be about 0.8 mg/kg, while the maximum tolerable dose would be about 50 mg/kg. However, based on the results of Experimental Test 8, and assuming a direct correlation between the metabolisms of mice and humans, preferred doses of naamidine might be expected to be within a range from about 25 mg/kg to about 50 mg/kg.

It should be understood that the preferred dose ranges extrapolated from the test data were based on an administration schedule of one dose per day. If the frequency of administering naamidine A in humans were increased, the preferred amount of drug per dose would be expected to decrease.

As for many drugs, it may be preferable to administer naamidine A along with a nontoxic, pharmaceutically acceptable carrier or diluent. Examples of suitable carriers or diluents are ethanol and cremaphor.

The present invention may be embodied in other specific forms without departing from its spirit of essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for inhibiting the growth of tumors which are dependent on epidermal growth factor, said method comprising the administration by injection to a person or animal in need of tumor growth inhibition of a pharmaceutical composition comprising substantially pure naamidine A and a nontoxic, pharmaceutically acceptable carrier or diluent, said naamidine A being present in an amount effective to inhibit the growth of tumors dependent on epidermal growth factor which are sensitive to treatment with naamidine A.

2. A method for inhibiting the growth of tumors which are dependent on epidermal growth factor according to claim 1, wherein said tumor-growth inhibiting amount of substantially pure naamidine A is within the range from about 0.08 mg to about 500 mg per kg of body mass of the human or animal in need of tumor growth inhibition.

3. A method for inhibiting the growth of tumors which are dependent on epidermal growth factor according to claim 1, wherein said tumor-growth inhibiting amount of substantially pure naamidine A is within the range from about 0.8 mg to about 50 mg per kg of body mass of the human or animal in need of tumor growth inhibition.

4. A method for inhibiting the growth of tumors which are dependent on epidermal growth factor according to claim 1, wherein said tumor-growth inhibiting amount of substantially pure naamidine A is within the range from between about 25 mg to about 50 mg per kg of body mass of the human or animal in need of tumor growth inhibition.

5. A method for inhibiting the growth of tumors which are dependent on epidermal growth factor according to claim 1, wherein said tumor-growth inhibiting amount of substantially pure naamidine A is nontoxic to the human or animal in need of tumor growth inhibition.

6. A method for inhibiting the growth of tumors which are dependent on epidermal growth factor according to claim 1, wherein said pharmaceutical composition is administered to the human or animal being treated once each day.

7. A method for inhibiting the growth of tumors which are dependent on epidermal growth factor according to claim 1, wherein said pharmaceutical composition is administered to the human or animal being treated once every 4 hours.

8. A method for inhibiting the growth of tumors which are dependent on epidermal growth factor according to claim 1, wherein said pharmaceutical composition is administered to the human or animal during the time until the cancerous tissue has been substantially fully treated.

9. A method for inhibiting the growth of tumors which are dependent on epidermal growth factor according to claim 1, wherein said pharmaceutically acceptable carrier or diluent comprises ethanol.

10. A pharmaceutical composition for inhibiting the growth of tumors which are dependent on epidermal growth factor and which are sensitive to said composition, said composition comprising a tumor-growth inhibiting amount of substantially pure naamidine A and a nontoxic, pharmaceutically acceptable carrier or diluent, wherein said pharmaceutically acceptable carrier or diluent comprises ethanol.

* * * * *

UNITED STATES PATENT AND TRADEMARK OFFICE
CERTIFICATE OF CORRECTION

PATENT NO. : 5,574,057

DATED : November 12, 1996

INVENTOR(S) : Chris M. Ireland, et al.

It is certified that error appears in the above-identified patent and that said Letters Patent is hereby corrected as shown below: Title page, item [57],     Abstract, final sentence, "squamous cells carcinoma" should be --squamous cell carcinoma--

Col. 6, Lines 33,34, "Perki-n Elmer" should be --Perkin-Elmer--

Col. 6, Line 40, "3C" should be --13C--

Col. 6, Line 45, "Dmax" should be --nmax--

Col. 6, Line 65, "over" should be --Over--

Col. 8, Line 12, "Proto-Oncogene  " should be --"Proto-Oncogene"--

Col. 8, Line 13, "of  ," should be --of--

Col. 8, Line 16, IC50(insutin)" should be --IC50(insulin)--

Col. 8, Line 20, "The criteria" should --directly follow the previous sentence--

Col. 10, Line 64, "o f" should be --of--

Signed and Sealed this

Twenty-ninth Day of July, 1997

*Attest:*

BRUCE LEHMAN

*Attesting Officer*     *Commissioner of Patents and Trademarks*